US00PP10126P

United States Patent [19]

Carruth

[11] Patent Number: Plant 10,126

[45] Date of Patent: Nov. 25, 1997

[54] FLORIBUNDA ROSE PLANT VARIETY NAMED 'WEKPLAPEP'

[75] Inventor: Thomas F. Carruth, Altadena, Calif.

[73] Assignee: Weeks Wholesale Rose Grower, Inc., Upland, Calif.

[21] Appl. No.: 673,065

[22] Filed: Jul. 1, 1996

[51] Int. Cl.[6] ..... A01H 5/00

[52] U.S. Cl. ..... Plt./22

[58] Field of Search ..... Plt./22, 11, 12, Plt./13

*Primary Examiner*—Howard J. Locker

*Attorney, Agent, or Firm*—Christie, Parker & Hale, LLP

[57] ABSTRACT

A new variety of floribunda rose suitable for garden decoration, having flowers of striped red and white coloration.

1 Drawing Sheet

BACKGROUND OF THE INVENTION

This invention relates to a new and distinct variety of floribunda rose. The varietal denomination of the new variety is 'Wekplapep'. The plant is a bushy upright seedling, cultivated for outdoor garden decoration. It has as its seed parent the variety known as 'Playboy' and its pollen parent the variety known as 'Jacraw'.

SUMMARY OF THE INVENTION

Among the features which distinguish the new variety from other presently available and known commercial rose cultivars are the following combination of characteristics: its unusual striped petal coloration whose patterns are different on the upper and under petal surfaces, its foliage with a somewhat quilted texture, its very dark red new growth, its blushed coloration on the underside of the mature leaflets, and its strong spice and rose fragrance. 'Wekplapep' may be asexually propagated by cuttings, budding or grafting.

Asexual reproduction of the new variety by budding as performed in Kern County and Upland, Calif., shows that the foregoing and other distinguishing characteristics come true to form and are established and transmitted through succeeding propagations.

COMPARISON WITH PARENTS

The new rose may be distinguished from its seed parent, 'Playboy' by the following combination of characteristics: whereas 'Playboy' produces a single petaled flowers of an orange blend coloration. 'Wekplapep' flowers are irregularly striped red and white and have significantly more petals, about 31 to 36. Whereas the new variety bears a textured foliage with a semi-glossy finish the foliage of the seed parent is less textured and has a very highly glossed finish.

The new variety may be distinguished from its pollen parent, 'Jacraw' by the following combination of characteristics: whereas 'Jacraw' bears medium sized flowers with only slight fragrance, 'Wekplapep' bears significantly larger flowers with a strong fragrance. 'Wekplapep' has a rounded mature plant habit of medium height, whereas 'Jacraw' has a more upright plant habit and is significantly taller.

BRIEF DESCRIPTION OF ILLUSTRATION

The accompanying photograph illustrates specimens of the new variety and shows the flowering thereof from bud to full bloom depicted in color as nearly correct as it is possible to make in a color illustration of this character. Throughout this specification, color values are based upon The Royal Horticultural Society Colour Chart, London, England, except where common terms of color definition are employed.

DESCRIPTION OF THE NEW VARIETY

The following description is of rose plants of the new cultivar grown outdoors in Upland, Calif. in the month of April. Phenotypic expression may vary with environmental, cultural and climatic conditions, as well as differences in conditions of light and soil.

Flower

The new variety bears its flowers sometimes singly, but usually in clusters of three to five or more per stem. Flowers are borne in irregular flat to rounded clusters on strong, medium to long stems (about 30 to about 38 cms.) for the class. Outdoors, the plant blooms nearly continuously during the growing season. The flowers have a strong damask and spicy fragrance.

Bud

The peduncle is of average to long length for the class (about 5 to about 7 cms.), and is usually erect. It is moderately rough, with many stipitate glands. Peduncle color is between 146B and 144B, sometimes lightly suffused with near 183B on the side facing the sun.

Before the calyx breaks, the bud is of medium size for the class (about 2 to about 2.5 cms. in diameter at the widest point), medium in length (about 2.5 to about 3 cms.), and pointed to globular in shape. The surface of the bud bears numerous stipitate glands usually with slender entire foliaceous parts extending beyond the tip of the bud equal to ¼ or more of its length. Bud color is between 146A and 137B, sometimes lightly suffused with near 183B on the side facing the sun.

The inner surface of the sepals is covered with fine wooly tomentum; sepal margins are lined with some stipitate glands and hairs.

As the petals open, the bud is medium to somewhat large for the class (about 2.5 to about 3 cms. in diameter at the widest point), medium in length (about 3 to about 3.5 cms.), and pointed to somewhat urn-shaped in form. The color of the under surfaces of the newly opened petals is irregularly striped and flecked with color ranging from between 4D and 155A to between 53B and 46A. Sometimes the white portion of the petal that is exposed to the sun blushes to between 54C and 48C. At the point where the petal attaches, there is a moderately large some of near 4D on the under surface. The color of the upper surfaces of the newly opened petals is irregularly striped and flecked with color ranging from between 155A and 4D to between 53A and 46A. At the point where the petal attaches, there is a moderately large zone of near 2C on the upper surface. The pattern of coloration on the under side of the petal differs from the pattern of coloration on the upper petal side. The bud opens up well and is generally not prevented from opening by wet, cold, hot or dry weather.

Bloom

When fully open, the bloom is moderately large for the class, ranging from about 9 to about 12 cms. in diameter with about 31 to 36 petals and about 2 to 5 petaloids regularly arranged. When partially open, the bloom form is somewhat cupped to high centered, and the petals are loosely spiraled to cupped with petal edges somewhat rolled under. When fully open, the bloom form is more cupped to somewhat globular, and the petals are somewhat undulated.

Petals

The petals are of medium thickness, with moderate substance. The upper surfaces are slightly velvety to satiny and under surfaces moderately shiny to satiny. The outer petals are nearly round to broadly obovate in shape with rounded apices. The inner petals are more narrowly obovate with rounded apices.

Newly Opened Flower

The under surface of the outer petals is irregularly striped and flecked with colors ranging from between 155A and 155B to between 60A and 53A. At the point where the petal attaches, there is a moderately large zone of between 2C and 4D on the under surface. The upper surface of the outer petals is irregularly striped and flecked with colors ranging from between 155B and 155A to between 53A and 46A. The white portion of the petal that is exposed to the sun sometimes blushes to between 63C and 55C. At the point where the petal attaches, there is moderately large zone of between 4C and 2D on the upper surface. The pattern of the coloration on the under side of the petal differs from the pattern of coloration on the upper petal side.

The coloration of the under and upper surfaces of the intermediate and inner petals is similar to the coloration of the under and upper surfaces of the outer petals but with less evidence of any blushing on the upper surface.

The general tonality of the newly opened flower is irregularly striped and flecked with colors ranging from between 155A and 155B to between 53A and 46A.

Three Day Old Flower

The under surface of the outer and inner petals is irregularly striped and flecked with color ranging from between 155D and 155B to between 61B and 53B. At the point where the petal attaches, there is a zone of between 155A and 4D on the upper surface. The upper surface of the outer petals is irregularly striped and flecked with color ranging from between 155D and 155B to between 60A and 53B. The white portion of the petal that is exposed to the sun sometimes blushes to between 64D and 63C. At the point where the petal attaches, there is zone of between 4C and 4D on the upper surface. The pattern of the coloration on the under side of the petal differs from the pattern of coloration on the upper petal side.

The general tonality of the three day old flower is irregularly striped and flecked with color ranging from between 155D to 155B to between 60A and 53B. The white portion of the petal that is exposed to the sun sometimes blushes to between 64D and 63C.

On the spent bloom, the petals usually drop off cleanly.

In April in Upland, Calif., blooms on the bush growing outdoors generally last from about three to four or more days. Cut roses grown outdoors and kept at normal indoor living temperatures generally last from about three to four or more days.

Male Reproductive Organs

Stamens are arranged regularly about the pistil, nominally about 30 stamens. The filaments are of uneven length, most with anthers. The anthers are moderately small for the class and all open approximately at the same time. Anther color is near 15A when immature and near 200B at maturity. Pollen is somewhat sparse and near 14C in color.

Female Reproductive Organs

Pistils vary in number (normally about 65). The styles are moderately even, short to average in length, average in caliper, and somewhat tightly bunched. Stigma color is near 2B. Style color is near 45D. Ovaries are usually all enclosed in the calyx.

Hips are moderately short in length, very globular in form, and near 25B in color when ripe. The hip surface is moderately smooth with moderately thick fleshy walls. The sepals fall away soon. Seeds are few to average in number (approximately 4 to 11).

Foliage

The compound leaves are comprised of three to five leaflets, occasionally seven leaflets, and are borne abundantly. The leaves are medium to large for the class (about 11 to about 13 cms. in length and about 9.5 to about 12 cms. in width at the widest point), moderately heavy and somewhat quilted in texture and semi-glossy in finish. The leaflets are moderately large for the class (about 4 to about 7 cms. in length and about 2.8 to about 4.5 cms. in width at the widest point), shaped broadly oval to somewhat ovate with acute to somewhat acuminate apices and round bases. Their margins are usually simply serrate.

The upper surface of the mature leaf is between 147A and 137A. The under surface of the mature leaf is between 147C and 138B, sometimes irregularly suffused with between 183C and 183D. The upper surface of the young leaf is between 146A and 173B, often heavily suffused with a color darker than between 187A and 183A. The under surface of the young leaf is between 146C and 138A, often heavily suffused with between 187B and 183A.

The rachis is average in caliper and moderately rough. The upper side is moderately grooved with many stipitate glands on the edges of the grooves. The under side of the rachis is moderately rough with many stipitate glands and few small prickles.

The stipules are medium to long in length with medium width somewhat short to medium straight points that usually turn out at an angle less than 45 degrees.

The plant displays an above average degree of resistance to powdery mildew and blackspot as compared to other commercial varieties grown under comparable conditions in Upland, Calif.

Growth

The plant has a bushy upright to rounded medium height habit (about 90 to about 120 cms. in height and about 80 to about 110 cms. spread at the widest point), with very full branching. It displays very vigorous growth and the canes are of medium caliper for the class.

The color of the major stems is near 146D. They bear some large prickles which are medium length for the class (about 0.8 to about 1.1 cms). The large prickles are almost straight, angled very slightly downward with a medium length moderately broad to rounded base; prickle color is near 165B.

The color of the branches is between 144A and 138A and have many large prickles which are of similar size and shape to the large prickles on the major stems; prickle color is near 161B, often lightly suffused with near 180C. The branches also have few small prickles of similar shape and coloration.

The color of the new shoots is between 144A and 138A, often heavily suffused on the side facing the sun with near 183B. They bear many large prickles which are of similar size and shape to the large prickles on the major stems; prickle color is near 183A. The shoots bear several small prickles of similar shape and coloration.

I claim:

1. Plants of a new and distinct variety of floribunda rose substantially as described and illustrated herein.

* * * * *

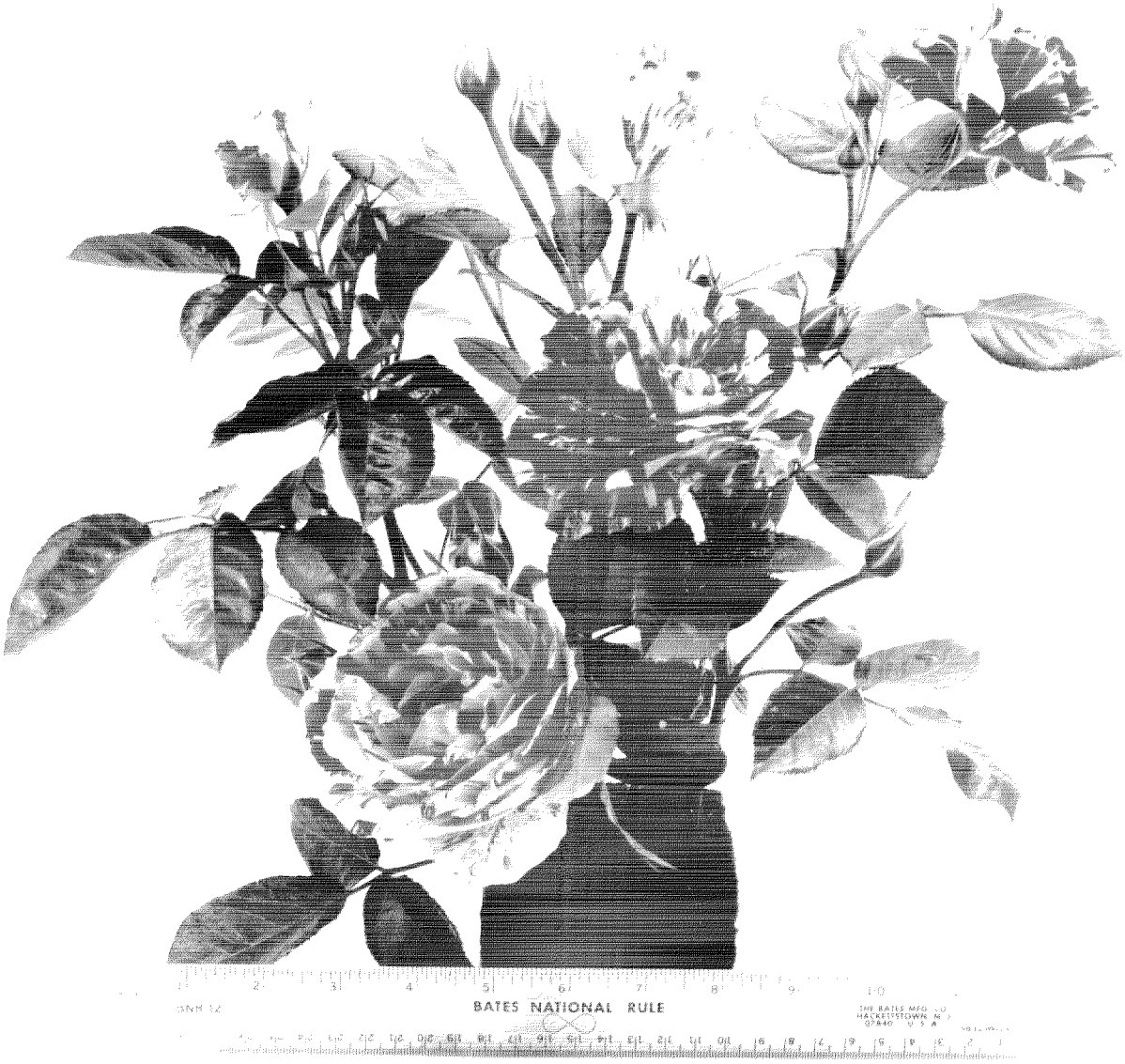
BATES NATIONAL RULE

UNITED STATES PATENT AND TRADEMARK OFFICE

CERTIFICATE OF CORRECTION

PATENT NO. : Plant 10,126
DATED : November 25, 1997
INVENTOR(S) : Thomas F. Carruth It is certified that error appears in the above-indentified patent and that said Letters Patent is hereby corrected as shown below:

Column 1, line 30, after "produces" delete "a".
Column 4, line 26, replace "normally" with -- nominally --.
Column 4, ine 56, replace "173B" with -- 137B --.

Signed and Sealed this

Second Day of June, 1998

*Attest:*

*Attesting Officer*

BRUCE LEHMAN

*Commissioner of Patents and Trademarks*